(12) United States Patent
Kahn et al.

(10) Patent No.: US 6,326,141 B1
(45) Date of Patent: *Dec. 4, 2001

(54) METHODS FOR DETERMINING RISK FOR TYPE I AND TYPE II DIABETES

(75) Inventors: C. Ronald Kahn, West Newton; Christine Reynet, Boston, both of MA (US)

(73) Assignee: Joslin Diabetes Center, Inc., Boston, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/996,565

(22) Filed: Dec. 23, 1997

Related U.S. Application Data

(60) Division of application No. 08/707,200, filed on Aug. 20, 1996, now Pat. No. 5,891,430, which is a division of application No. 08/076,089, filed on Jun. 11, 1993, now Pat. No. 5,589,374, which is a continuation-in-part of application No. 07/901,710, filed on Jun. 19, 1992, now abandoned.

(51) Int. Cl.[7] .................... C12Q 1/68; G01N 33/53; C07H 21/04

(52) U.S. Cl. .................... 435/6; 435/7.1; 536/23.2; 536/23.5

(58) Field of Search .................... 435/6, 7.1; 536/23.2, 536/23.5

(56) References Cited

U.S. PATENT DOCUMENTS

| | | | |
|---|---|---|---|
| 5,179,017 | 1/1993 | Axel et al. | 435/240.2 |
| 5,621,075 * | 4/1997 | Kahn | 530/350 |

OTHER PUBLICATIONS

Taylor, S.I. et al. Mutations in insulin–receptor gene in insulin–resistant patients. Diabetes Care 13(3):257–279, Mar. 1990.*

Ho, L.T. et al. Insulin insensitivity in offspring of parents with type 2 diabetes mellitus. Diabetic Medicine 7:31–34, 1990.*

Bell, G. Diabetes 40:413–422, Apr. 1991.*

Ianuzzo, C.D. et al. Biochemical and Biophysical Research Communications 58(1):107–111, 1974.*

Dillmann, W.H. et al. Clinical Research 31(2):384A, 1983.*

Alexander et al., "Insulin stimulates glyceraldehyde–3–phosphate dehydrogenase gene expression through cis–acting DNA sequences", *Proceeding of the National Academy of Sciences*, vol. 85, pp. 5092–5096, (1988).

Arner et al., "Defective insulin receptor tyrosine kinase in human skeletal muscle in obesity and Type 2 (non–insulin–dependent) diabetes mellitus", *Diabetologia*, vol. 30, pp. 437–440, (1987).

Arora et al., "Glucose Phosphorylation in Tumor Cells", *J. Biol. Chem.*, vol. 265, No. 11, pp. 6481–6488, (1990).

Baron et al., "Rates and tissue sites of non–insulin–and insulin–mediated glucose uptake in humans", *Am. J. Physiol.*, vol. 255, pp. E769–E774, (1988).

Beck–Nielsen, "Insulin Resistance in Skeletal Muscles of Patients with Diabetes Mellitus", *Diabetes/Metabolism Reviews*, vol. 5, No. 6, pp. 487–493, (1989).

(List continued on next page.)

Primary Examiner—Carla J. Myers
Assistant Examiner—Diana Johannsen
(74) Attorney, Agent, or Firm—Fish & Richardson P.C.

(57) ABSTRACT

Purified DNA including a sequence encoding Diabetogene rad.

14 Claims, 5 Drawing Sheets

OTHER PUBLICATIONS

Beguinot et al., "Differentiation–Dependent Phosphorylation of a 175,000 Molecular Weight Protein in Response to Insulin and Insulin–Like Growth Factor–I in L6 Skeletal Muscle Cells", *Endocrinology,* vol. 125, pp. 1599–1605, (1988).

Bell et al., "Gene for non–insulin–dependent diabetes mellitus (maturity–onset diabetes of the young subtype) is linked to DNA polymorphism on human chromosome 20Q", *Proceedings of the National Academy of Sciences,* vol. 88, pp. 1484–1488, (1991).

Bogardus et al., "Correlation between Muscle Glycogen Synthase Activity and In Vivo Insulin Action in Man", *J. Clin. Invest.,* vol. 73, pp. 1185–1190, (1984).

Bogardus et al., "Distribution of In Vivo Insulin Action in Pima Indians as Mixture of Three Normal Distributions", *Diabetes,* vol. 38, pp. 1423–1432, (1989).

Caro et al., "Insulin Receptor Kinase in Human Skeletal Muscle from Obese Subjects with and without Noninsulin Dependent Diabetes", *J. Clin Invest.,* vol. 79, pp. 1330–1337, (1987).

Daniel et al., "Insulin–Stimulated Entry of Glucose Into Muscle In Vivo as a Major Factor in the Regulation of Blood Glucose", *J. Physiol.,* vol. 247, pp. 273–288, (1975).

Dugail et al., "Adipose–tissue–specific increase in glyceraldehyde–3–phosphate dehydrogenase activity and mRNA amounts in sucking pre–obese Zucker rats", *Biochem J.,* vol. 254, pp. 483–487, (1988).

Felber et al., "Role of Lipid Oxidation in Pathogenesis of Insulin Resistance of Obesity and Type II Diabetes", *Diabetes,* vol. 36, pp. 1341–1350, (1987).

Felber et al., "Carbohydrate and Lipid Oxidation in Normal and Diabetic Subjects", *Diabetes,* vol. 26, pp. 693–699, (1977).

Freymond et al., "Impaired Insulin–stimulated Muscle Glycogen Synthase Activation In Vivo in Man Is Related to Low Fasting Glycogen Synthase Phosphatase Activity", *J. Clin. Invest.,* vol. 82, pp. 1503–1509, (1988).

Froguel et al., "Close linkage of glucokinase locus on chromosome 7p to early–onset non–insulin–dependent diabetes mellitus", *Nature,* vol. 356, pp. 162–164, (1992).

Hother–Nielsen et al., "Enhanced hepatic insulin sensitivity, but peripheral insulin resistance in patients with Type1 (insulin–dependent) diabetes", *Diabetologia,* vol. 30, pp. 834–840, (1987).

Jaenisch et al., "Transgenic Animals", *Science,* vol. 240, pp. 1468–1472, (1988).

Kahn and White et al., "The Insulin Receptor and the Molecular Mechanism of Insulin Action", *J. Clin. Invest.,* vol. 82, pp. 1151–1156, (1988).

Kimball et al., *Diabetes/Metabolism Reviews,* vol. 4, pp. 773–787, (1988).

Klip and Pâquet, "Glucose Transport and Glucose Transporters in Muscle and Their Metabolic Regulation", *Diabetes Care,* vol. 13, No. 3, pp. 228–243, (1990).

Knowler et al., "Diabetes Mellitus in the Pima Indians: Incidence, Risk Factors and Pathogenesis", *Diabetes/Metabolism Reviews,* vol. 6, pp. 1–27, (1990).

Leighton and Cooper, "The role of amylin in the insulin resistance of non–insulin–dependent diabetes mellitus", *Trends Biochem. Sci.,* vol. 15, pp. 295–299, (1990).

Mandarino et al., "Effects of Insulin Infusion on Human Skeletal Muscle Pyruvate Dehydrogenase, Phosphofructokinase, and Glycogen Synthase", *J. Clin. Invest.,* vol. 80, pp. 655–663, (1987).

Minchenko and Germanyuk, "Effect of Hydrocortisone on the Expression of Mitochondrial Genes in the Liver of Normal and Alloxan Diabetic Rats", *Endocrinologia Experimentalis.,* vol. 18, pp. 3–18, (1984).

Mosthaf et al., "Altered expression of insulin receptor types A and B in the skeletal muscle of non–insulin–dependent diatetes mellitus patients", *Proceedings of the National Academy of Sciences,* vol. 88, pp. 4728–4730, (1991).

Nankervis et al., "Impaired insulin action in newly diagnosed Type 1 (insulin–dependent) diabetes mellitus", *Diabetologia,* vol. 27, pp. 497–503, (1984).

Obermaier–Kusser et al., "A Deffective Intramolecular Autoactivation Cascade May Cause the Reduced Kinase Activity of the Skeletal Muscle Insulin Receptor from Patients with Non–insulin–dependent Diabetes Mellitus", *J. Biol. Chem.,* vol. 264, No. 16, pp. 9497–9504, (1989).

Persons et al., "Increased Expression of Glycolysis–Associated Genes in Oncogene–Transformed and Growth–Accelerated States", *Mol. Carcinogenesis,* vol. 2, pp. 88–94, (1989).

Sambrook and Maniatis, Molecular Cloning A Laboratory Manual, cold Spring Harbot Laboratory Press, (Cold Spring Harbor, NY), pp. 10.38–10.50, (1989).

Shatzman et al., "Expression, Identification, and Characterization of Recombinant Gene Products in *Escherichia coli*", *Methods in Enzymology,* vol. 152, pp. 661–673, (1987).

Smith et al., "Genes Tranfered by Retroviral Vectors into Normal and Mutant Myoblasts in Primary Cultures are Expressed in Myotubes", *Molecular and Cellular Biology,* vol. 10, No. 6, pp. 3268–3271, (1990).

Sugden et al., "Substrate interactions in the development of insulin resistance in Type II diabetes and obesity", *J. Endocrinol.,* vol. 127, pp. 187–190, (1990).

Vionnet et al., "Nonsense mutation in the glucokinase gene causes early–onset non–insulin–dependet diabetes mellitus", *Nature,* vol. 356, pp. 721–722, (1992).

Wallberg–Henriksson, "Acute exercise:fuel homeostasis and glucose transport in insulin–dependent diabetes mellitus", *Med Sci. Sports Exerc.,* vol. 21, pp. 356–361, (1989).

Chavrier et al, "Molecular Cloning of YPTI/SEC4–Related cDNAs from an Epithelial Cell Line", *Mol. Cell Biol.,* 10(12): 6578–6585, (1990).

Bell et al., "Molecular biology of mammalian glucose transporters", *Diabetes Care* 13:198–208 (1990).

Bergman, "Toward physiological understanding of glucose tolerance" *Diabetes* 38:1512–1527 (1989).

Bogardus, "Perspective: does insulin resistance primarily affect skeletal muscle?" *Diabetes/Metabolism Reviews* 5:527–528 (1989).

Bourey et al., "Effects of altered glucose homeostasis on glucose transporter expression in skeletal muscle of the rat", *J. Clin. Invest.,* 86:542–547 *(1990).*

Brands et al., "The primary structure of the alpha subunit of human elongation factor 1. structural aspects of guanine nucleotide–binding sites" *Eur. J. Biochem.* 155(1):167–71 (1986).

Carlson et al., "Isolation and mapping of a polymorphic DNA sequence for human muscle glycogen phosphorylase (pMCPMP1) on chromosome 11 [PYGM]" *Nuc. Acids Res.* 16:10403 (1988).

Caro et al., "Cellular alterations in liver, skeletal muscle and adipose tissue responsible for insulin resistance in obesity and type II diabetes", *Diabetes/Metabolism Reviews* 5:665–689 (1989).

Colosia et al., "Induction of rat liver 6–phosphofructo–2–kinase/fructose–2,6–biphosphatase mRNA by refeeding and insulin", *J. Biol. Chem.* 263:18669–18677 (1988).

DeFronzo, "The triumvirate:β–cell, muscle, liver/a collusion responsible for NIDDM", *Diabetes* 37:667–845 (1988).

Duguid et al., "Isolation of cDNAs of scrapie–modulated RNAs by subtractive hybridization of a cDNA library" PNAS, USA, 85:5738–5742 (1988).

Ericksson et al., "Early metabolic defects in persons at increased risk for non–insulin–dependent diabetes mellitus" *N.E.J. Medicine* 321:337–343 (1989).

Feng et al., "Effect of diabetes on glutamine synthetase expression in rat skeletal muscles", *Amer. J. of Physiology* 258:E762–E766 (1990).

Foley, "Mechanisms of impaired insulin action in isolated adipocytes from obese and diabetic subjects" *Diabetes/Metabolism reviews* 4:487–505 (1988).

Gomez–Foix et al., "Adenovirus–mediated transfer of the muscle glycogen phosphorylase gene into hepatocytes confers altered regulation of glycogen metabolism" *J. Biol. Chem.* 267:25129–34 (1992).

Griffiths et al., "Diabetes–induced changes in guaninenucleotide–regulatory–protein mRNA detected using synthetic oligonucleotide probes", *Eur.J. Biochem.* 193:367–374 (1990).

Ho et al., "Insulin insensitivity in offspring of parents with type 2 diabetes mellitus" *Diabetic Medicine* 7:31–34 (1990).

Hollenbeck et al., "Variations in insulin–stimulated glucose uptake in healthy individuals with normal glucose tolerance", *J. Clin. Endocrinology and Metabolism* 64:1169–1173 (1987).

Knowler et al., "Diabetes mellitus in the pima Indians: incidence, risk factors and pathogenesis", *Diabetes/Metabolism Reviews* 6:1–27 (1990).

Leaman et al., "Insulin–like growth factor–I and –II messenger RNA expression in muscle, heart, and liver of streptozotocin–diaetic swine", *Endocrinology* 126:2850–2857 (1990).

Lillioja et al., "Insulin resistance in pima Indians", *Acta Med. Scand. Suppl.* 723:103–19 (1987).

Lillioja et al., "In vivo insulin action is familial characteristic in nondiabetic pima Indians", *Diabetes* 36:1329–1335 (1987).

Liu et al., "Subtractive cloning of a hybrid human endogenous retrovirus and calbindin gene in the prostate cell line PC3", *Cancer Research* 51:4107–4110 (1991).

Mohn et al., "The immediate–early growth response in regenerating liver and insulin–stimulated H–35 cells: comparison with serum–stimulated 3T3 cells . . . ",*Molecular/Cellular Biology* 11:381–390 (1991).

Mohn et al., Immediate–early gene expression differs between regenerating liver, insulin–stimulated H–35 cells, and mitogen–stimulated BALB/C 3T3 cells, *J. Biol. Chem.* 265:21914–21921 (1990).

Mueckler, "Family of glucose–transporter genes/implications for glucose homeostasis and diabetes", *Diabetes* 39:6–11 (1990).

Olefsky et al., "Cellular mechanisms of insulin resistance in non–insulin dependent (Type II) diabetes", *Amer. J. Med.* 85(suppl 5A):86–105 (1988).

Pedersen et al., "Evidence against altered expression of GLUT1 or GLUT4 in skeletal muscle of patients with obesity of NIDDM", *Diabetes* 39:865–870 (1990).

Popovich et al., "Diabetes decreases creatine kinase enzyme activity and mRNA level in the rat heart", *Amer. J. Physiology* 257:E573–E577 (1989).

Reaven, "Role of insulin resistance in human disease", *Diabetes* 37:1595–1607 (1988)., Reynet et al, "RAD: a novel member of the RAS–GTPase family over–expressed in muscle to type II diabetic humans" (abstract) *J. Cell. Biochem. Suppl. O* (18 part A) 143 (1994).

Schweinfest et al., "Subtraction hybridization cDNA libraries from colon carcinoma and hepatic cancer", *Genet. Annal. Techn. Appl.* 7:64–70 (1990).

Sivitz et al., "Regulation of glucose transporter messenger RNA in insulin–deficient states", *Nature* 340:72–74 (1989).

Strout et al., "Vanadate treatment of streptozotocin diabetic rats restores expression of the insulin–responsive glucose transporter . . . ", *Endocrinology* 126:2728–2732 (1990).

Tindall et al., "Fidelity of DNA synthesis by the thermus aquaticus DNA polymerase" *Biochemistry* 27:6008–6013 (1988).

Travis et al., "Subtractive cloning of complementary DNAs and analysis of messenger RNAs with regional heterogeneous distributions in primate cortex", *Neuropharmacology* 26:845–854 (1987).

Uetsuki et al., "Isolation and characterization of the human chromosomal gene for polypeptide chain elongation factor–1.alpha", *J. Biol. Chem.* 264:5791–8 (1989).

Walker et al., "Insulin and glucose–dependent regulation of the glucose transport system in the rat L6 skeleton muscle cell line" *J. Biol. Chem.* 264:6587–6595 (1989).

Warram et al., "Slow glucose removal rate and hyperinsulinemia precede the development of type II diabetes in the offspring of diabetic parents", *Am. College of Physicians* 113:909–915 (1990) Yoo et al., "Cloning, expression and characterization of the human transcription elongation factor, TFIIS", *Nuc. Acids Res.* 19:1073–9 (1991).

Yoo et al., "Cloning, expression and characterization of the human transcription elongation factor, TFIIS" *Nuc. Acid Res.* 19:1073–9 (1991).

* cited by examiner

```
       1                    21                    41
       GTGGCTGCAG  CAGCAGCGGC  GGCGGAAACC  CTAAAGTCCG  AGTCCGGACT  ACGAG
1: .......... .......... .......... .......... .......... .....

61                    81                   101
       TGCGT  GGCCTCCTAA  TCCGGATCCT  AGTCCTGAGC  GTGTCTGTGT  GCGAGTGGAC
1: ..... .......... .......... .......... .......... ..........

121                              141
       GGTCCCGGAC  GCG  ATG  ACC  CTG  AAC  GGC  GGC  GGC  AGC  GGA  GCG  GGC
1: .......... ...  met  thr  leu  asn  gly  gly  gly  ser  gly  ala  gly 161                              181                          20
       GGG  AGC  CGC  GGT  GGG  GGC  CAG  GAG  CGC  GAG  CGC  CGT  CGG  GGC  AGC
1: gly  ser  arg  gly  gly  gly  gln  glu  arg  glu  arg  arg  arg  gly  ser 1                             221                             241
       ACA  CCC  TGG  GGC  CCC  GCC  CCG  CCG  CTG  CAC  CGC  CGC  AGC  ATG  CCG
1: thr  pro  trp  gly  pro  ala  pro  pro  leu  his  arg  arg  ser  met  pro 261                              281
       GTG  GAC  GAG  CGC  GAC  CTG  CAG  GCG  GCG  CTG  ACC  CCG  GGT  GCC  CTG
1: val  asp  glu  arg  asp  leu  gln  ala  ala  leu  thr  pro  gly  ala  leu 301                              321
       ACG  GCG  GCC  GCG  GCC  GGG  ACG  GGG  ACC  CAG  GGT  CCC  AGG  CTG  GAC
1: thr  ala  ala  ala  ala  gly  thr  gly  thr  gln  gly  pro  arg  leu  asp 341                              361                      38
       TGG  CCC  GAG  GAC  TCC  GAG  GAC  TCG  CTC  AGC  TCA  GGG  GGC  AGC  GAC
1: trp  pro  glu  asp  ser  glu  asp  ser  leu  ser  ser  gly  gly  ser  asp 1                             401                              421
       TCA  GAC  GAG  AGC  GTT  TAC  AAG  GTG  CTG  CTG  CTG  GGG  GCG  CCC  GGC
1: ser  asp  glu  ser  val  tyr  lys  val  leu  leu  leu  gly  ala  pro  gly 441                              461
       GTG  GGC  AAG  AGC  GCC  CTG  GCG  CGC  ATC  TTC  GGC  GGT  GTG  GAG  GAC
1: val  gly  lys  ser  ala  leu  ala  arg  ile  phe  gly  gly  val  glu  asp 481                              501
       GGG  CCT  GAA  GCA  GAG  GCA  GCA  GGG  CAC  ACC  TAT  GAT  CGC  TCC  ATT
1: gly  pro  glu  ala  glu  ala  ala  gly  his  thr  tyr  asp  arg  ser  ile
```

FIG. 3A

```
        521                              541                                 56
    GTA GTG GAC GGA GAA GAG GCA TCA CTC ATG GTC TAC GAC ATT TGG
1:  val val asp gly glu glu ala ser leu met val tyr asp ile trp 1                        581                          601
    GAG CAG GAC GGG GGC CGC TGG TTG CCC GGC CAC TGC ATG GCC ATG
1:  glu gln asp gly gly arg trp leu pro gly his cys met ala met 621                          641
    GGG GAT GCC TAT GTC ATT GTG TAC TCA GTG ACG GAC AAG GGC AGC
1:  gly asp ala tyr val ile val tyr ser val thr asp lys gly ser 661                           681
    TTC GAG AAG GCC TCA GAA CTG CGG GTC CAG CTG CGG CGT GCA CGG
1:  phe glu lys ala ser glu leu arg val gln leu arg arg ala arg 701                          721                              74
    CAA ACA GAT GAT GTG CCC ATC ATC CTC GTG GGC AAC AAG AGC GAC
1:  gln thr asp asp val pro ile ile leu val gly asn lys ser asp 1                        761                          781
    CTG GTG CGC TCT CGT GAG GTC TCG GTG GAT GAG GGC CGG GCC TGC
1:  leu val arg ser arg glu val ser val asp glu gly arg ala cys 801                          821
    GCG GTG GTC TTT GAC TGC AAG TTC ATT GAG ACA TCA GCG GCA TTG
1:  ala val val phe asp cys lys phe ile glu thr ser ala ala leu 841                          861
    CAC CAC AAT GTC CAG GCG CTG TTT GAA GGT GTC GTG CGC CAG ATA
1:  his his asn val gln ala leu phe glu gly val val arg gln ile 881                          901                              92
    CGC CTG CGC AGG GAC AGC AAA GAA GCC AAC GCA CGA CGG CAA GCA
1:  arg leu arg arg asp ser lys glu ala asn ala arg arg gln ala 1                        941                          961
    GGC ACC CGG AGG CGA GAG AGC CTT GGC AAA AAG GCG AAG CGC TTC
1:  gly thr arg arg arg glu ser leu gly lys lys ala lys arg phe 981                          1001
    TTG GGC CGC ATC GTA GCT CGT AAC AGC CGC AAG ATG GCC TTT CGC
1:  leu gly arg ile val ala arg asn ser arg lys met ala phe arg 1021                         1041
    GCC AAA TCC AAG TCC TGC CAC GAC CTC TCG GTT CTC TAG GTCCCACC
1:  ala lys ser lys ser cys his asp leu ser val leu ***  ........

1061             1081              1101
    CG CTCCCACTAT GGTGGGAGAC GAACGGAAGG GTTGGTGGGC TGGCCCAGCC AA
1:  .. .......... .......... .......... .......... .......... ..
```

FIG. 3B

```
                1121              1141                  1161
     CTGCCCCG GGTGCCTCAG AGCAGGCTCA GACTCTGGGT CCCTCGGAGC TGCCAGC
  1: ........ .......... .......... .......... .......... .......

1181                1201                          1
     CGG GCACCCCCAA CCTCATGGTC ATGGACAGAT AGACAGTGCT GCCCTGCGAA G
  1: ... .......... .......... .......... .......... .......... .

221              1241              1261
     TGGCTCTCA GGGGCCAGTG AGGGCTGGGC CCACAGAGAT GCATGCGCAG GCTCAT
  1: ......... .......... .......... .......... .......... ......

1281           1301              1321
     ATGC GTCCCAAGCA GCCGCAGCGC AGCCGCCGGG CAGGCCTGCG TGCCGGGAGA
  1: .... .......... .......... .......... .......... ..........

1341              1361                  1381
     GGACTCTGCC TTTTTTCACA GCCCGGGTGT GCCTGCCCTG GAGGGAGGCT CTTCA
  1: .......... .......... .......... .......... .......... .....

1401              1421
     GTGCG GTAGCTACTT GTTTACATGC AGATTTTTGT AATAAAGGCT ATTTCCTGAT
  1: ..... .......... .......... .......... .......... ..........

1441
     AAA
  1: ...
     (SEQ ID NO: 1)
```

FIG. 3C

METHODS FOR DETERMINING RISK FOR TYPE I AND TYPE II DIABETES

This application is a divisional application of Ser. No. 08/707,200 filed on Aug. 20, 1996, U.S. Pat. No. 5,891,430 which is a divisional application of Ser. No. 08/076,089 filed on Jun. 11, 1993; U.S. Pat. No. 5,584,374 which is a continuation in part application of Ser. No. 07/901,710 filed on Jun. 19, 1992, abandoned. The contents of all of the aforementioned application(s) are hereby incorporated by reference.

BACKGROUND OF THE INVENTION

The invention relates to the genetic basis of diabetics.

Diabetes mellitus is among the most common of all metabolic disorders, affecting up to 11% of the population by age 70. Type I (insulin dependent diabetes mellitus or IDDM) diabetes represents about 5 to 10% of this group and is the result of a progressive autoimmune destruction of the pancreatic β-cells with subsequent insulin deficiency. Type II (non-insulin dependent diabetes mellitus or NIDDM) diabetes represents 90–95% of the affected population but is much less well understood from the point of view of primary pathogenesis. Type II diabetic patients exhibit elements of both insulin resistance and relative insulin deficiency.

Alterations in glucose homeostasis are the sine qua non of diabetes mellitus and occur in both the Type I and Type II forms of the disease. In the mildest forms of diabetes this alteration is detected only after challenge with a carbohydrate load, while in moderate to severe forms of disease hyperglycemia is present in both the fasting and postprandial states. The most important tissue involved in disposal of a glucose load following oral ingestion, i.e., in the absorptive state, is skeletal muscle. (Klip 1990 *Diabetes Care* 13:228–243; Caro et al. 1989 *Diab. Metab. Rev.* 5:665–689; Bogardus 1989 *Diab. Metab. Rev.* 5:527–528; Beck-Nielsen 1989 *Diab. Metab. Rev.* 5:487–493) Skeletal muscle comprises 40% of the body mass, but has been estimated to account for between 80 and 95% of glucose disposal at high insulin concentration or following an oral glucose load. (Beck-Nielsen 1989; Baron et al. 1988 *Am. J. Physiol.* 255:E769–74) In insulin-treated animals, about 25% of an intravenous glucose load enters muscle within 1 minute. (Daniel et al. 1975 *J. Physiol.* (Lond) 247:273–288).

Skeletal muscle takes up glucose by facilitated diffusion in both an insulin-independent and insulin-dependent manner and has been shown to express relatively high levels of GLUT4 (the "insulin responsive" glucose transporter) and low levels of GLUT1 and GLUT3 (the transporters believed to be involved in basal glucose transport). (Mueckler 1990 *Diabetes* 39:6–11; Bell et al. 1990 *Diabetes Care* 13:198–208) Once inside the muscle, glucose is rapidly phosphorylated by hexokinase to form glucose 6-phosphate. Although the rate-limiting step for glucose uptake is at the level of transport, there is increasing evidence that the major control of carbohydrate metabolism is exerted after the glucose-6-phosphate step. (Mandarino 1989 *Diab. Metab. Rev.* 5:474–486; Felbert et al. 1977 *Diabetes* 26:693–699) Depending on the hormonal milieu and metabolic state, the glucose 6-phosphate can enter either anabolic or catabolic pathways. The major anabolic pathway involves conversion of the glucose to glycogen. The rate-limiting enzyme of this reaction is glycogen synthase. The activity of glycogen synthase is regulated primarily by phosphorylation and dephosphorylation and the presence of the allosteric regulator glucose-6-phosphate, although the level of expression of the enzyme must also play a role. In catabolic states, glucose is metabolized through the glycolytic pathway to pyruvate which in turn is either converted to lactate (under anaerobic conditions) or is oxidized by $CO_2$ and acetyl-CoA. The latter reaction is catalyzed by the multienzyme complex pyruvate dehydrogenase (PDH). PDH activity is also regulated by the level of the enzyme, phosphorylation and dephosphorylation, and a number of allosteric modifiers. Most of the enzymes and proteins involved in glucose metabolism have been identified and purified, and over the past several years, several of these have been cloned at a molecular level.

The dominant hormone regulating glucose metabolism in muscle is insulin. Insulin exerts its actions through insulin, and to a lesser extent IGF-1, receptors, both of which are expressed in skeletal muscle. (Beguinot et al. 1989 *Endocrinology* 125:1599–1605; Sinha et al. 1987 *J. Clin. Invest.* 79:1330–1337; Obermaier-Kusser et al. 1989 *J. Biol. Chem.* 264:9497–9504; Arner et al. 1987 *Diabetologia* 30:437–440) Like insulin and IGF-1 receptors on other tissues, these receptors are protein tyrosine kinases which are stimulated upon insulin and IGF-1 binding. (White et al. *J. Clin. Invest.* 82:1151–1156) This initial insulin signal then acts through a cascade of events involving phosphorylation and dephosphorylation, as well as possible mediator generation to promote glucose uptake, stimulate metabolism and conversion of glucose to glycogen by activating glycogen synthase, and regulate a variety of intracellular enzymes involved in carbohydrate. (Yki-Jarvinen et al. 1987 *J. Clin. Invest.* 80:95–100; Mandarino et al. 1987 *J. Clin. Invest.* 80:655–663) In addition, insulin also acts at the level of muscle to modify lipid and protein metabolism through effects on membrane transport, enzyme activity and gene expression. (Kimball et al. 1988 *Diab. Metab. Rev.* 4:773–787; Alexander et al. 1988 *Proc. Natl. Acad. Sci. USA* 85:5092–5096).

In both Type I and Type II diabetes there are major alterations in the ability of peripheral tissues to take up and metabolize glucose. (DeFronzo 1988 *Diabetes* 37:667–687; Olefsky et al. 1988 *Am. J. Med.* 85:86–105; Reaven 1988 *Diabetes* 37:1595–1607; Nankervis et al. 1984 *Diabetologia* 27:497–503; Yki-Jarvinen et al. 1986 *N. Engl. J. Med.* 315:224–230; Hother-Nielsen et al. 1987 *Diabetologia* 30:834–840) These alterations affect liver, fat and muscle, as well as other tissues. In Type I diabetes, the alterations in glucose metabolism are largely secondary to insulin deficiency which has both acute and chronic effects with regard to regulation of glucose uptake and intracellular disposition metabolism. (Nankervis 1984; Yki-Jarvinen 1986; Hother-Nielsen 1987) The exact basis for impaired metabolism in muscle of Type II diabetics is less clear, but probably involves a combination of factors including a significant level of insulin resistance (due to acquired or genetic factors), as well as some component of relative insulin deficiency.

In obesity and diabetes, there are a variety of alterations in the muscle glucose homeostasis. In obese individuals without diabetes the major alteration is in oxidative glucose metabolism. (Beck-Nielsen 1989; DeFronzo 1988; Olefsky 1988) There are reduced insulin-stimulated nonoxidative glucose metabolism, a reduction in both basal and insulin-stimulated glucose oxidation and a higher rate of lipid oxidation than in lean controls. (Felber et al. 1987 *Diabetologia* 26:1341–1350) Glycogen synthase activity is decreased in obese individuals and may contribute to the reduced nonoxidative glucose disposal. (Bogardus et al. 1984 *J. Clin. Invest.* 73:1185–1190; Freymond et al. 1988 *J.*

*Clin. Invest.* 82:1503–1509) In obese diabetics both oxidative and nonoxidative pathways are altered, and the latter may play a more quantitatively important role. (Beck-Nielsen 1989) In both obesity and Type II diabetes there is also decreased insulin stimulated receptor phosphorylation (Caro 1987; Obermaier-Kusser 1989; Arner 1987) decreased insulin stimulated glucose transport (Caro 1987; Felber 1987) decreased insulin-stimulated pyruvate dehydrogenase activity (Mandarino 1989), and defective insulin-stimulated glycogen synthase. (Mandarino 1989; Freymond 1988; Thorburn et al. 1990 *J. Clin. Invest.* 85:522–529) Untreated Type I diabetic humans and rodents show many of the same changes. (Nankervis 1984; Yki-Jarvinen 1986; Hother-Nielsen 1987; Wallberg 1989 *Med. Sci. Sports. Exerc.* 21:356–361) In the latter group, these tend to reverse with proper therapy, although in most studies some reduction in insulin-stimulated glucose oxidation and insulin-stimulated PDH activity persist despite therapy. Factors mediating these alterations in glucose homeostasis in diabetes and obesity are multiple and include the altered hormonal milieu, altered substrate levels, and possibly even circulating insulin antagonists. (DeFronzo 1988; Sugden et al. 1990 *J. Endocrinol.* 127:187–190; Leighton et al. 1990 *Trends Biochem. Sci.* 15:295–299) A summary of the defects in glucose metabolism in muscle in Types I and II diabetes and obesity is given in reference 4.

Although controversy exists as to the primary defect in Type II diabetes several studies suggest that the earliest detectable abnormality may be in glucose disposal by muscle. (Bogardus 1989; DeFronzo 1988; Reaven 1988; Lilloja et al. 1988 *Acta Med. Scand. Suppl.* 723:103–119; Ho et al. 1990 *Diabetic Med.* 7:31–34; Eriksson et al. 1989 *N. Engl. J. Med.* 321:337–343; Bogardus et al. 1989 *Diabetes* 38:1423–1432; Lilloja et al. 1987 *Diabetes* 36:1329–1335; Knowler et al. 1990 *Diab. Metab. Rev.* 6:1–27; Warram et al. 1990 *Ann. Int. Med.* 113:909–915; Martin et al. Submitted for publication) In a study initiated by Dr. J. Stuart Soeldner over 20 years ago, over 200 offspring of two Type II diabetic parents were identified and evaluated for abnormalities in glucose tolerance, glucose disposal and insulin secretion (Warram 1990; Martin) 155 of the offspring were normoglycemic at the onset of study. The individuals were subsequently followed for an average of 14 years during which time 25 developed Type II diabetes. Analysis of data gathered at entry to the study provided a unique insight as to the earliest defects detectable in prediabetic individuals. This study revealed that there were no differences in either first or second phase insulin secretory capacity in these offspring which predicted the development of diabetes. However, overall glucose disposal rate was reduced. Based on the Bergman model of glucose disposal (Bergman 1989 *Diabetes* 38:1512–1527), this decrease in glucose disposal rate was due to reduced insulin sensitivity ($S_1$) and insulin independent glucose disposal ($S_G$). Low values of $S_1$ and/or $S_G$ were highly predictive of the subsequent development of diabetes. (Warram 1990; Martin) If one compares the normoglycemic offspring in this study with the lowest quintile of insulin sensitivity to those offspring in the highest quintile of insulin sensitivity, there was a 62-fold increase in relative risk of developing Type II diabetes during follow-up (see preprint of Martin in Appendix). Likewise low glucose sensitivity (which reflects both insulin-independent and basal insulin-dependent glucose disposal) increased the relative risk of diabetes by 22-fold.

Similar findings and conclusions have been derived from studies of the Pima Indian population which has a very high incidence of Type II diabetes. (Lilloja 1988; Ho 1990; Erikkson 1989; Bogardus 1989; Lilloja 1987; Knowler 1990) In addition, in this population, evidence has been presented that insulin sensitivity is inherited in family clusters and with a pattern of distribution suggestive of an autosomal dominant trait. (Bogardus 1989; Lilloja 1987) Alterations in glucose metabolism and glycogen synthase activity can also be detected in biopsies from prediabetic Pima Indians prior to onset of clinical diabetes. (Knowler 1990; Warram 1990; Martin; Bergman 1989; Foley 1988 *Diabet. Metabl. Rev.* 4:487–505) Consistent with the hypothesis that Type II diabetes develops in the presence of an underlying defect in insulin sensitivity are the many observations which indicate that aggressive insulin therapy in the Type II diabetic may normalize blood glucose and glycohemoglobin, but usually fails to reverse completely the insulin resistance which is observed in this disease. (DeFronzo 1988; Olefsky 1988) Genetic variability in insulin sensitivity may also exist in the non-diabetic Caucasian populations (Hollenbeck et al. 1987 *J. Clin. Endocrinol. Metab.* 64:1169–1173), suggesting that genes which control insulin sensitivity may exist at some frequency in control non-diabetic, as well as diabetic, population.

Although there is considerable evidence for alterations in the metabolism and the activity of a variety of enzymes and transporters in muscle in diabetes mellitus, including changes in insulin receptors, glucose transporters, glycogen synthase and pyruvate dehydrogenase, there is less information concerning specific alterations in the expression of the genes for these proteins or other proteins which might account for the altered insulin action. Alterations in the level of mRNA for the insulin-sensitive glucose transporter GLUT4, but not GLUT1, have been observed in skeletal muscle of streptozotocin diabetic rats and are restored toward normal by insulin or vanadate treatment. (Bourey 1990 *J. Clin. Invest.* 86:542–547; Strout et al. 1990 *J. Endocrinology* 126:2728–2732; Sivitz 1989 *Nature* 340:72–74). Insulin and glucose have also been shown to regulate glucose transporter mRNA expression in the cultured skeletal muscle cell line L6. (Walker et al. 1989 *J. Biol. Chem.* 264:6587–6595) In both rodent and human models of obesity and Type II diabetes, the data on glucose transporter mRNA expression are more controversial with some studies showing altered levels of GLUT4 expression in adipose tissue, but not muscle, and others showing alterations in both tissues. (Caro 1989; Pedersen 1990 *Diabetes* 39:865–870) Diabetes has also been shown to affect the level of expression of insulin-like growth factors I and II in muscle (Leaman 1990 *Endocrinology* 126:2850–2857), creatine kinase (Popovich 1989 *Amer. J. Physiol* 257:E573–E577), glutamine synthetase (Feng 1990 *Am. J. Physiol.* 258:E762–E766), and the α-subunit of guanin-nucleotide regulatory protein, $G_S$. (Griffiths et al. 1990 *Eur. J. Biochem.* 193:357–364) By contrast, mRNA for the important bifunctional enzyme 6-phosphofructo-2-kinase/fructose-2, 6-bisphosphatase is altered in liver of STZ diabetic rats, but is not altered in muscle. (Colosia 1988 *J. Biol. Chem.* 263:18669–18677) Some investigators have also shown a change in expression of one of the alternatively spliced forms of the insulin receptor in muscle of human with Type II diabetes, although this apparently occurs without a significant change in level of total receptor mRNA. (Mosthaf et al. 1991 *Proc. Natl. Acad. Sci. USA* 88:4728–4730) Levels of total mRNA and those of most of the major structural proteins like actin do not appear to be altered in diabetes. (Pedersen 1990) Little or no data yet exist for effects of diabetes on the mRNA levels in muscle for glycogen synthase, PDH, hexokinase, the insulin receptor substrate (IRS-1) etc., although gene probes now exist for a number of these important metabolic enzymes. (Persons et al. 1989 *Mol. Carcinog.* 2:88–94; Dugail 1988 Biochem. J. 254:483–487; Arora et al. 1990 *J. Biol. Chem.* 65:6481–6488; Minchenko et al. 1984 Endocrinol. Exp. 18:3–18; Sun et al. 1991 *Nature* 352:73–77)

SUMMARY OF THE INVENTION

In general, the invention features purified DNA including a sequence encoding the Diabetogene rad. A diabetogene is a gene whose expression, at the mRNA level, is altered (i.e., is different from what is seen in a normal individual) in an individual with diabetes and/or obesity. Rad encodes a new member of the ras/GTPase related gene family. Rad shares 45–55% homology at the nucleotide level and 33% homology at the amino acid level with other members of this family in the GTPase domain, but has additional 5' and 3' coding sequences compared to the low molecular weight GTP-binding proteins. Rad was formerly referred to as Diabetogene C9D6. The invention also includes: a vector including a DNA sequence encoding Diabetogene rad; a cell, e.g., a cultured cell, e.g., a muscle cell, containing purified Diabetogene rad DNA; a cell capable of giving rise to a transgenic animal; a cell capable of expressing a polypeptide encoded by Diabetogene rad; an essentially homogeneous population of cells, each of which includes the purified Diabetogene rad DNA.

In another aspect, the invention features a substantially pure preparation of a polypeptide encoded by rad. The invention also includes a purified preparation of an antibody, e.g., a monoclonal antibody, directed against rad.

In another aspect, the invention features a therapeutic composition comprising a diabetogene product, e.g., the rad protein, and a pharmaceutically acceptable carrier.

In another aspect, the invention features a method for manufacture of the rad protein comprising culturing a cell transformed with rad DNA in a medium to express the protein.

In another aspect, the invention features a method for treating an animal (e.g., a human afflicted with Type I or Type II diabetes, or an experimental animal, e.g., an animal model for a disease or disorder, e.g., a NOD mouse, an ob/ob mouse, a db/db mouse, a Zucker fatty rat, or a streptozotocin induced rat) having a disease characterized by a deficiency or an excess in a diabetogene product including, administering a therapeutically-effective amount of the diabetogene product (in the case of a deficiency) or an inhibitor of production or function of the diabetogene product (in the case of an excess) to the animal.

In another aspect, the invention features a method of evaluating the effect of a treatment including administering the treatment and evaluating the effect of the treatment on the expression of a diabetogene. In preferred embodiments, the treatment is administered to: an animal, e.g., a human afflicted with Type I or Type II diabetes; an experimental animal, e.g., an animal model for a disease or disorder, e.g., a NOD mouse, an ob/ob mouse, a db/db mouse, a Zucker fatty rat, or a streptozotocin induced rat, or a transgenic animal carrying a diabetogene, e.g., a Diabetogene rad transgene; or a cell, e.g. a cultured cell, e.g., a cultured muscle cell.

In preferred embodiments: the expression of the diabetogene is increased in Type II diabetes (and preferably not increased in Type I diabetes); the diabetogene is the gene for muscle glycogen phosphorylase, the gene encoded by clone F2D8 (see below), or the gene for elongation factor 1α; the expression of the diabetogene is not elevated in Type I diabetes; the diabetogene is Diabetogene rad; the expression of the diabetogene is decreased in Type II diabetes; the expression of the diabetogene is increased in normal individuals; the expression of the diabetogene is decreased in normal individuals; the expression of the diabetogene is increased in Type I diabetes.

In another aspect, the invention features a method for determining if a subject is at risk for a glucose related disorder, e.g., diabetes or obesity, including examining the subject for the expression of a diabetogene, non-wild type expression being indicative of risk.

In preferred embodiments: the expression of the diabetogene is increased in Type II diabetes (and preferably not increased in Type I diabetes); the diabetogene is the gene for muscle glycogen phosphorylase, the gene encoded by clone F2D6, or the gene for elongation factor 1α; the expression of the diabetogene is not elevated in Type I diabetes; the diabetogene is Diabetogene rad; the expression of the diabetogene is decreased in Type II diabetes; the expression of the diabetogene is increased in normal individuals; the expression of the diabetogene is decreased in normal individuals; the expression of the diabetogene is increased in Type I diabetes.

In another aspect, the invention features a method for determining if a subject is at risk for a glucose related disorder, e.g., diabetes or obesity, including providing a nucleic acid sample from the individual and determining if the structure of a diabetogene differs from wild type, departure from wild type indicating risk. In preferred embodiments: the determination includes determining if the diabetogene has a gross chromosomal rearrangement, e.g. by blot analysis; the determination includes sequencing the diabetogene; the subject is a human; the subject is a NOD mouse, an ob/ob mouse, a db/db mouse, a Zucker fatty rat, or a streptozotocin induced rat.

In preferred embodiments: the expression of the diabetogene is increased in Type II diabetes (and preferably not increased in Type I diabetes); the diabetogene is the gene for muscle glycogen phosphorylase, the gene encoded by clone F2D6, or the gene for elongation factor 1α; the expression of the diabetogene is not elevated in Type I diabetes; the diabetogene is Diabetogene rad; the expression of the diabetogene is decreased in Type II diabetes; the expression of the diabetogene is increased in normal individuals; the expression of the diabetogene is decreased in normal individuals; the expression of the diabetogene is increased in Type I diabetes.

In another aspect, the invention features a method of evaluating an animal model for a disorder or disease state, e.g., a glucose related disorder, e.g., diabetes or obesity, including determining if a diabetogene in the animal model is expressed at a predetermined level. In preferred embodiments, the predetermined level is lower than the level in wild type or normal animal; the predetermined level is higher than the level in a wild type or normal animal.

In another aspect, the invention features a transgenic rodent, e.g. a mouse, hamster, or rat, having a transgene which includes a diabetogene, e.g., Diabetogene rad. In preferred embodiments, the transgenic diabetogene is a mutant form, e.g., a deletion mutant, of the gene.

In another aspect, the invention features a method of screening for a diabetogene including: (a) supplying a cDNA library enriched for diabetes-specific cDNA molecules; (b) supplying a cDNA library enriched for normal cDNA molecules; and (c) hybridizing the normal-enriched and the diabetes-enriched cDNA libraries with a probe. Differential hybridization of the probe to the normal-enriched and the diabetes-enriched libraries is indicative of a diabetogene. In preferred embodiments the method further includes hybridizing any differentially hybridizing probe from step (c) to RNA from a diabetic individual and RNA from a non-diabetic individual to confirm the differential expression of the differentially hybridizing probe.

Substantially pure DNA is DNA that is not immediately contiguous with both of the coding sequences with which it is immediately contiguous (i.e., one at the 5' end and one at the 3' end) in the naturally-occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other DNA sequences. It also includes a recombinant DNA which is part of a hybrid gene encoding additional polypeptide sequence.

Homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

A transgene is defined as a piece of DNA which is inserted by artifice into a cell and becomes a part of the genome of the animal which develops from that cell. Such a transgene may be partly or entirely heterologous to the transgenic animal.

A transgenic animal, e.g., a transgenic mouse, is an animal having cells that contain a transgene, which transgene was introduced into the animal, or an ancestor of the animal, at an embryonic stage.

A substantially pure preparation of a polypeptide is a preparation which is substantially free of the proteins with which it naturally occurs in a cell.

The invention is useful for: investigating the basis of glucose metabolism in normal and disease states at the levels of gene structure and gene expression (mRNA or protein); determining if a subject is at risk for a glucose-metabolism related disorder, e.g., diabetes, e.g., Type II diabetes; evaluating the effect of a treatment, e.g., a treatment for a glucose-metabolism related disorder, e.g., diabetes, on the level of expression of a diabetogene; evaluating animal models on the basis of whether, at the level of diabetogene expression, the model resembles a human disorder; and making transgenic animals and genetically altered cell lines for use in research.

Other features and advantages of the invention will be apparent from the following description and from the claims.

DETAILED DESCRIPTION

The drawings are first briefly described.

Drawings

FIG. 3 is the cDNA and deduced amino acid sequence of human rad.

PREPARATION OF LIBRARIES

Preparation of Normal and Type II cDNA Libraries cDNA libraries were prepared using skeletal muscle mRNA from one normal and one Type II diabetic individual, see Sambrook et al. 1989 *Molecular Cloning: A Laboratory Manual* Cold Spring Harbor Press, N.Y. The decision to use single individuals for library construction was based on the possible heterogeneity of Type II diabetes and fear that genetically-related alterations in gene expression in this disease could be obscured by pooling of samples. The cDNA was prepared using oligo-dT primers and ligated into Lambda-Zap II (Stratagene) using EcoRI adapters. Lambda-Zap II contains the coding sequences for Bluescript flanked by the filamentous phage initiation and termination sequences, allowing in vivo excision of the inserts in Bluescript in the presence of a helper virus. The titers of the unamplified and amplified libraries were $\sim 2 \times 10^6$ and $\sim 2 \times 10^{10}$, respectively, for both the diabetic and normal muscle samples.

Muscle samples of a size sufficient for large scale RNA extraction were obtained at surgery for amputation, frozen in liquid nitrogen and extracted for RNA using the guanidium isothiocyanate method. (Chomcyznski et al. 1987 *Anal. Biochem.* 162:156–159) Clinical data on the metabolic state of the patient, the type and duration of diabetes and any complications which might exist were recorded. Great care was taken to obtain the muscle samples as rapidly and cleanly as possible to avoid any degradation of mRNA. All samples were dissected from the viable margin of the limb from either quadriceps or gastrocnemius muscle. In humans, these muscles are comprised of both red and white fibers, as well as other cell types (particularly vascular cells) which may have differing patterns of gene expression. (Klip 1990) As individual clones are selected in the subtraction process, it will be ultimately important to validate that these are indeed products of muscle and that differences between diabetics and non-diabetics are not due to differences in muscle type studied or to some underlying complication of diabetes, such as uremia or infection. Since multiple samples will be used for the screening Northern blots in which the muscle type and patient history are know, many of these differences (as well as genetic differences in humans) should be detected.

Figure 1:
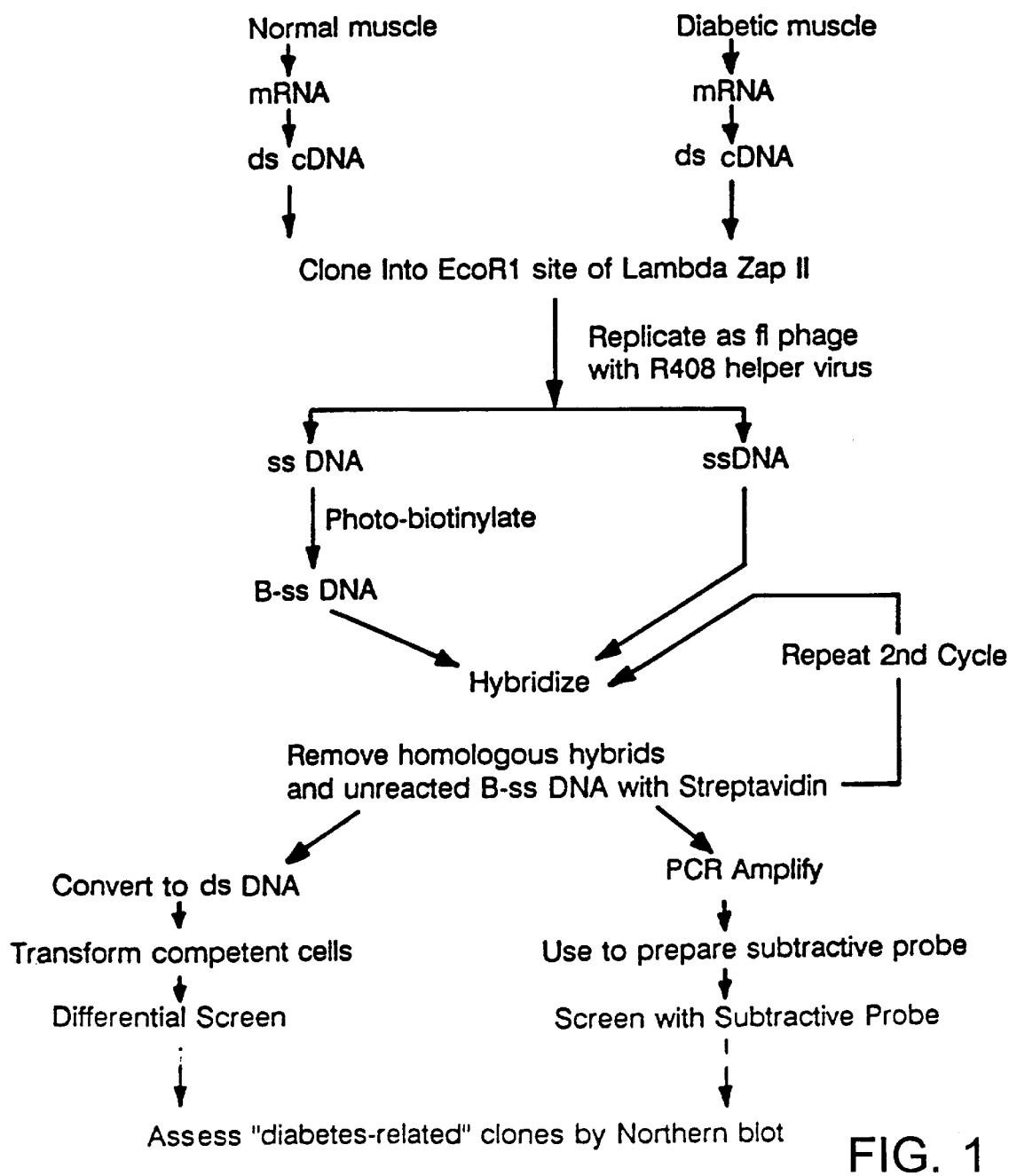
FIG. 1 is a diagram of the screening method of the invention.

Preparation of a Library Enriched in Normal cDNAs and of a Library Enriched in Type II Specific cDNAs As initial step to identify genes whose expression was increased or decreased in Type II diabetes, two subtraction libraries were prepared, one enriched in normal cDNAs and one enriched in diabetic cDNAs, using a modification of the procedure of Schweinfest, et al. (Schweinfest et al. 1990 *Genet. Anal. Techn. Appl.* 7:64–70) and InVitrogen. The overall strategy is outlined in FIG. 1. Initially, single-stranded DNA was prepared from the normal and the Type II cDNA libraries using R408 helper phage. The single-stranded DNA was isolated by polyethylene glycol precipitation and purified by repeated phenol, chloroform-phenol and chloroform extractions and, in some cases, further purified on a CsCl gradient. (Druguid et al. 1988 *Proc. Natl.*

*Acad. Sci. USA* 85:5738–5742) When analyzed by agarose gel electrophoresis and ethidium bromide staining, the ss-DNA migrated a broad band from 1.6–4 kb reflecting the range of size of ss-pBluescript plus varying length inserts. In addition there was a discrete band at ~4 kb representing the helper phage DNA. A total of 120–150 µg of ss-DNA was isolated from each cDNA library.

Approximately 60 µg of each ss-DNA preparation was biotinylated using Photoprobe biotin (Vector Laboratories). Specifically, 30 µg of DNA was dissolved in 30 µl Hepes-EDTA buffer, sonicated for 1 minute and boiled for 3 min to shear and denature the DNA, mixed with 60 µl Photoprobe biotin (0.5 mg/ml), and exposed to light from a 275 W sunlamp at 10 cm for 15 min. The reaction was quenched by addition of Tris-HCl, and the unreacted biotin removed by repeated extraction with 2-butanol. The biotinylated DNA was precipitated with ethanol and resuspended in $dH_2O$.

To prepare a library enriched for genes preferentially expressed in normal muscle, 3 µg of ss-DNA from normal muscle was mixed with 30 µg of biotinylated ss-DNA from the diabetic muscle along with 3 µg of polyA and polyc and co-precipitated with ethanol on dry ice. The resultant pellet was resuspended in 10 µl $dH_2O$, diluted with an equal volume of 2× hybridization buffer (In Vitrogen) and incubated at 68° for 40–48 hours. The hybrids of normal-diabetic DNA, as well as the unhybridized biotinylated "diabetic" DNA, were then removed using two extractions with streptavidin and one extraction with Vectrix Avidin (avidin coupled to polysaccharide polymer). The enriched normal ss-DNA was then subjected to a second round of subtraction using the same protocol. Based in studies using labeled DNA, two rounds of subtraction with a 10-fold excess of DNA produce a ~95% depletion of cDNA species common to both libraries and a 20-fold enrichment of selected cDNAs.

A second subtraction library enriched for genes preferentially expressed in diabetic muscle was prepared in an analogous manner using ss-DNA from diabetic muscle and biotinylated ss-DNA from the normal muscle library. Both subtracted libraries were then converted to double stranded libraries by incubation with DNA polymerase and ligase in the presence of an appropriate primer (T3) and a mixture of oligonucleotides.

A library from a Type I diabetic, as well as a muscle library from a normal or diabetic individual using random primed cDNA can also be made. The Type I library could be used as the subtractor with the Type II library to help isolate cDNAs whose expression is altered in Type II diabetes specifically. Subtraction is most efficient using oligo-dT libraries since all cDNAs have the same "relative starting point". A normal muscle library prepared using random primers (rather than oligo-dT) would be useful for getting full length sequence of clones detected in oligo-dT libraries. As described above the cDNA libraries can be constructed using Lambda Zap II with EcoRI adapters.

Availability of the Type I muscle library will allow preparation of additional subtraction libraries and/or subtraction probes as described herein. Further modifications of the screening techniques described herein can help narrow down the clones for screening and therefore yield more important clones. For example, the Type II diabetes-enriched library would be more likely to yield specific Type II "diabetogenes" if the subtraction is conducted using a Type I diabetic ss-DNA preparation against a Type II diabetic ss-DNA preparation, rather than a ss-DNA preparation from a non-diabetic individual. In addition, it may be describable to increase the number of rounds of substraction to further enhance the library for diabetes-related genes, and to use a Type I diabetes enriched subtractive probe to further screen the dot-blots. (see below)

Screening for Diabetogenes

Initial Screening Strategy

An aliquot (1/40) of each subtraction library was used to transform competent XL-1 Blue cells (Stratagene) and plated on a media enriched with ampicillin, X-Gal and IPTG. For the "normal-enriched" library this aliquot of the library yielded about 700 colonies; for the "diabetes-enriched" library this aliquot yielded about 450 colonies. Thus, the calculated library sizes are ~28,000 and ~18,000 for the "normal" and "diabetes" enriched libraries, respectively. In both cases about 87% of the colonies were white indicating the presence of inserts. Duplicate colony lifts were prepared using BioTrans nylon membranes (ICN) form each dish of cells. One lift was hybridized to a cDNA probe prepared from the normal RNA and the other to a cDNA probe prepared from the diabetic RNA. (Sambrook 1989) About 30 colonies of interest were defined in the aliquot of the normal-enriched library by differential hybridization, and 19 colonies with differential hybridization were identified in the aliquot of the diabetes-enriched library. Each of these was then picked and expanded to a 5 ml mini-prep culture. DNA was isolated using the method of Maniatas (Sambrook 1989), subjected to a restriction digest with EcoRI and analyzed by electrophoresis in 0.7% agarose. Almost all isolates contained inserts, varying in size from 0.4–2 kb. The gels of these restriction digests were prepared in duplicate and subjected to Southern blotting for an additional round of differential screening using cDNA probes from the normal and diabetic RNA samples. Some inserts hybridized well to both probes, some hybridized poorly to both probes and some showed differential hybridization suggestive that these were truly representative of genes differentially expressed in two muscle samples.

It was clear from preliminary experiments that the most difficult and time consuming portion of this method is the screening of the subtraction library for clones of interest. Two of the major limitations of subtraction library analysis have already been alluded to and are (a) the failure of the procedure to remove completely some of the most abundant cDNA species and (b) the difficulty in identifying very rare messages with this approach. Two (or even three) rounds of subtraction may not eliminate common messages (which may still account for a significant percentage of the subtraction clones), and it is quite possible that some of the messages of interest may be non-abundant (such as receptors or signaling molecules). To help overcome these problems, the screening strategy was modified as described below, by using subtracted probes to analyze replicate dot blots of the colonies of the library. (Tindall et al. 1988 *Biochemistry* 27:6008–6013; Erlich 1989 *PCR Technology: Principles and Applications for DNA Amplifications*. M. Stockton Press, N.Y.)

Improved Dot-Blot Screening Strategy

During the initial screening process, several technical problems were identified which appeared to limit the application of this method and produce false positives, as well as false negatives. First, although duplicate colony lifts can be produced from a single plate, they tend to be quite variable as to the amount of the colony (and hence cDNA) which adheres to the filter. Using a velvet template to replicate plate the dishes improved reproducibility somewhat but was still suboptimal. Secondly, the bacterial plates were not optimal for long-term storage. After the potential positives were identified, and picked, the plates could be kept at 4° C. for several weeks, but tended to deteriorate or exhibit contamination if kept for months. Thus, except for the colonies which were picked, the library was lost for further screening. A third problem was the inability of differential screening to identify rarer mRNAs (cDNAs) in the library which might represent differentially expressed and metabolically important species, since screening with total cDNA probes favors finding differences in more abundant mRNA species. A fourth problem, related to the two previous problems, was that since the clones not picked could not be stored for long periods of time, it was impossible to return to the library to search for the cDNAs representing rarer mRNAs which were indeed differentially expressed.

To help overcome these problems, a colony screening strategy was developed which provided for good duplicate filters, long-term storage of all colonies, and improved sensitivity for low abundance DNAs. Thus, after transformation, each colony was picked using a sterile toothpick and used to inoculate a single well of a 96-well plate. After initial growth, a replicate of this "archive" plate was made by the inoculation of bacterial cells from each well of the plate using a 96-well replicator beaded lid (FAST system, Falcon). The wells of the archive plate were then diluted to a final concentration of 20% glycerol, and the plates stored at −70° C. Duplicate dot-blots were prepared from the copy plate (after allowing the infected bacterial to grow to high density) using a dot-blot manifold and BioTrans nylon membranes (ICN).

To overcome the difficulty in identifying rare messages, a method was developed to screen the dot-blots of the subtracted libraries using subtracted probes. Beginning with a small aliquot of dsDNA or ssDNA of each of the subtraction libraries as templates, subtracted probes were prepared by the polymerase chain reaction (PCR) using SK and KS primers (since all inserts are in pBluescript). Under the proper conditions of time and concentration, there was no difficulty in obtaining very high efficiency amplification of inserts up to 2 kb in size which can then be cut with EcoRI to remove the polylinker and used as templates for random prime labeling to give high specific activity subtracted probes. To minimize the background created by some labeling of the polylinker, unlabeled pBluescript DNA digested with KpnI was added to the hybridization buffer, or the polylinker was removed from the EcoRI digests using spin columns.

Duplicate dot-blots, from the "diabetic-enriched" colonies hybridized with a "normal" subtracted probe and a "diabetic" subtracted probe, (right side) were prepared. very good quality replicate filters were obtained. Clones which were strongly positive with the diabetic probe and negative with the normal probe were found. Screening of about 1/6 of the two subtraction libraries (this represents ~2,000 colonies from the "normal" enriched library and ~1,700 colonies from the diabetes enriched library) resulted in the discovery of 23 normal and 21 diabetic colonies which appeared to be differentially expressed. About half of these (11 normal and 10 diabetic) were regarded as highly positive and had inserts on the plasmid preparation. In addition, on this initial screen about 190 and 140 colonies from each library gave a signal too low on both filters to determine possible differential expression. These presumably represent less abundant mRNAs which may or may not be differentially expressed but may represent some of the most interesting cDNAs from a metabolic point of view. Since all of the colonies have been saved in the archive plate, it will now be possible to prepare fresh duplicate dot-blot filters to analyze these less abundant mRNAs/cDNAs.

Analysis of Differential Clones for Insert and Differential Expression by Northern Blots Following identification on the dot blots using the subtracted probes, each of the candidate clones was expanded to a 30 ml culture, and the plasmid DNA isolated and analyzed by restriction digest with EcoRI. This yields sufficient DNA for electrophoretic analysis, purified insert for labeling of up to 4 Northern blots and sequence analysis. The inserts varied in size from 0.4 to 2.0 kb (Table 1) and were purified by agarose gel electrophoresis and Gene Clean II. The most important step of initial characterization of these subtraction libraries is to determine which of these presumptive differential clones are truly representative of "diabetes-related" changes in gene expression, which are simply due to individual variation and which are specific to Type II versus Type I diabetes. To this end, screening Northern blots were prepared using RNA (20 µg) samples from several normal and diabetic individuals (both Type II and Type I). These blots can be hybridized using random primed probes prepared from the isolated inserts of the differential colonies to determine the true pattern of expression.

Figure 2:
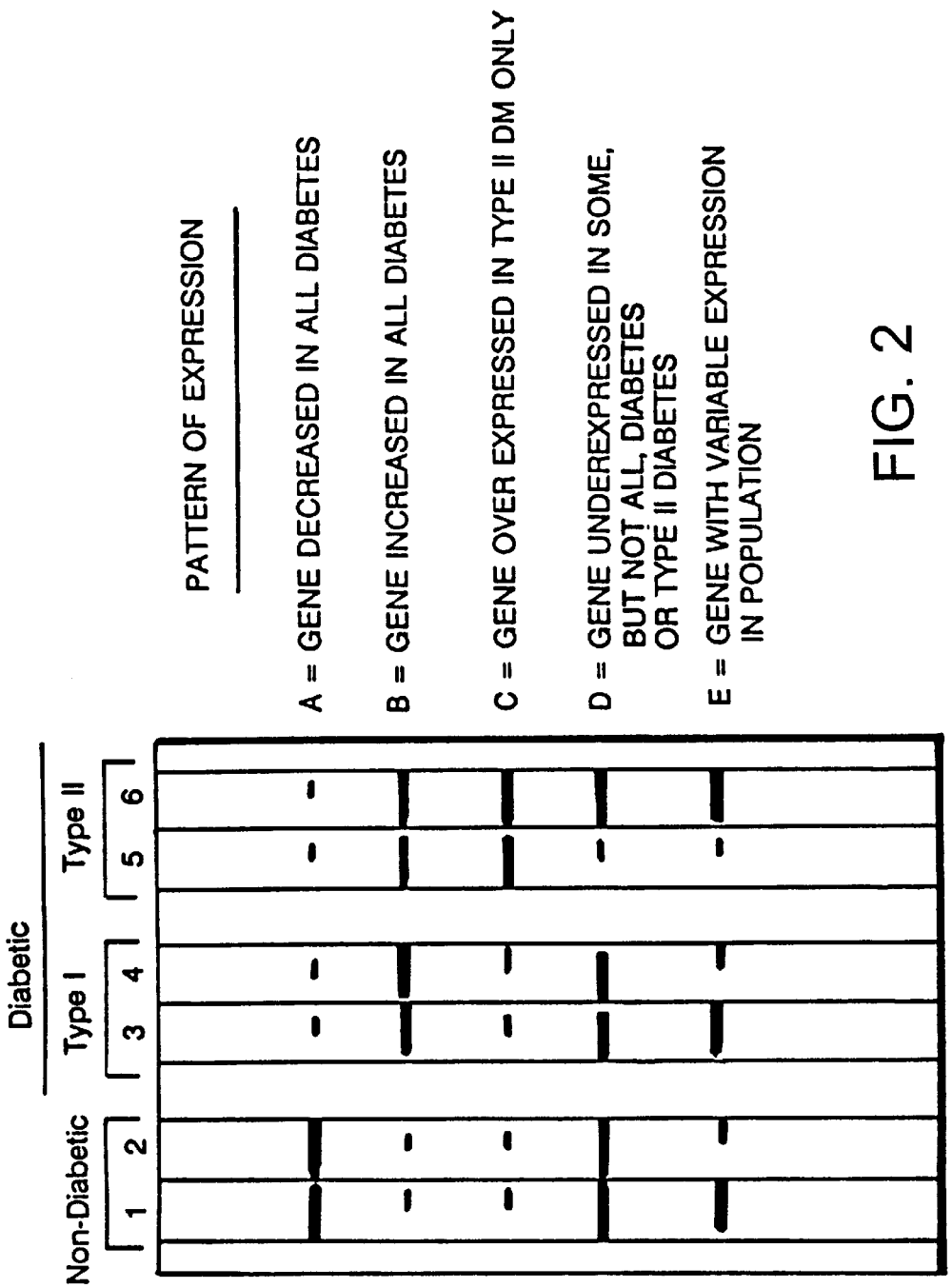
FIG. 2 is a diagram of theoretical patterns of diabetogene expression.

A schematic showing the various predicted patterns of expression is shown in FIG. 2. Five types of patterns were expected and are illustrated in this schematic. Some probes will fail to show differential hybridization at this stage despite showing differential properties in the earlier stages of screening (Pattern E). These represent mRNAs which are variable in the population or abundant mRNAs which were not removed by subtraction, but are not truly differentially expressed. Other probes might recognize messages preferentially expressed in normals (Pattern A), mRNAs preferentially expressed in both Types I and II diabetics (Pattern B), or RNAs preferentially expressed in some or all Type II diabetics only (Patterns C and D). These patterns help to identify those mRNA species whose expression might be altered in all patients with diabetes, and this represent some general metabolic alteration, versus those differences in gene expression which are primarily due to insulin deficiency and hence expressed predominantly in Type I diabetes or due to insulin resistance and expressed predominantly in Type II diabetes. Some clones would be expected to show variable expression in the diabetics if the expression is related to level of control, or other metabolic or genetic variables.

Of the initial 21 clones studied at the Northern stage, 2 were enriched in normals (for example clone G5N7) and 7 were enriched in diabetes (for example, clones B10D6 and C9D6). (See Table I) Note that clone B10D6 appears to represent an mRNA species which is preferentially overexpressed in all diabetics, where clone rad represents a species overexpressed primarily in Type II diabetics.

Despite all previous efforts at selection, approximately 30% of clones were non-differential at this stage.

TABLE I

Potential Diabetes-Related Clones

| Identification | Insert Size[‡] (kb) | mRNA size (kb)[†] | Expression in Diabetes | Sequence/ Homology |
|---|---|---|---|---|
| B1D4 | 0.7 | 2.6 (4.6) | Increased | Muscle glycogen phosphorylase |
| B10D6 | 1.5 | 2 (4.2) | Increased | Human elongation factor 1α |
| G2D8 | 0.5 | 3.3, 2.5 | Increased | No hit in GeneBank |

TABLE I-continued

Potential Diabetes-Related Clones

| Identification | Insert Size‡ (kb) | mRNA size (kb)† | Expression in Diabetes | Sequence/ Homology |
|---|---|---|---|---|
| B14D7 | 1.7 | N.D. | Increased | not done |
| F2D8 | 0.4 | 2.8 (6.4) | Increased | mitochondrial |
| C9D6 (rad) | 0.8 | 3.8, 1.4 | Increased | no hit in Genebank |
| C8N8 | 0.4 | 2.8 (6.4) | Increased | Same as F2D8 |
| N13 | 0.4 | 7, 1.6 | Decreased | Human myosin |
| G5N7 | 1.0 | ~1 kb | Decreased | Human myoglobin |
| D55 | 1.0 | 7.0 | Variable | No hit in Gene Bank |
| C12N2 | 1.0 |  | Variable | No hit in Gene Bank |
| D5N4* | 1.8 |  | Variable | E. coli. β-galactosidase |
| C1N4 | 1.0 |  | Variable | E. coli. β-galactosidase |
| D5N3 | 0.2, 0.4, 0.7 |  | Variable | Alu a |
| A8N6 | 1.1 |  | Variable | Not done |
| C4N7 | 0.5 |  | Variable | Not done |
| C5D7 | 2.0 |  | Variable | Not done |

*six other similar clones identified
†minor species are in parenthesis
‡EcoRI digests Characterization of Diabetes-Related Clones Once a clone which shows one of the "diabetes-related" patterns by Northern analysis described above has been identified characterization will include sequencing, comparison to genetic data banks for homology or identity to known DNA and protein sequences, analysis of pattern of expression in human and rodent tissues, and ultimately preparation of anti-peptide antibodies for study of protein expression and function. Depending on the number of such clones, it may be desirable to prioritize their evaluation. Prioritization will largely depend on information obtained in the screening Northern blots. Highest priority can be given to a given class e.g., to the class of clones expressed differentially in Type II diabetes only (such as clone C9D6 in Table I) on clones showing the greatest differential levels of expression.

Clones can be sequenced on both strands with Sequenase (United States Biochemicals) using initially T3 and T7 primers. Other specific primers selected at convenient intervals to allow construction of a complete cDNA sequence can be used. It is likely that most inserts will not represent full length clones, and thus, to obtain full-length sequence of interesting clones, it will be necessary to screen the original libraries and the random-primed muscle cDNA library for related cDNAs, and in turn, to sequence these. All sequences should be analyzed using the EUGENE and SAM programs.

Sequencing and Identification of Differential Clones

Potential positive clones from the screens described above were expanded to 30 ml cultures and the plasmid DNA were isolated using Qiagen mini-prep columns. The DNA was then digested by EcoRI and the insert size determined by agarose gel electrophoresis as described above. Partial sequence data was then obtained from the isolated DNA using T3 and T7 primers and Sequenase (United States Biochemicals).

A summary of the insert size, differential expression, and sequence data is presented in Table I. Thus far, limited sequence data are available on 9 clones, all of which have been compared to genetic data banks for homology to known DNA and protein sequences using the SAM and EUGENE programs.

Two of the clones over-expressed represent metabolic enzymes not previously studies at the RNA level in diabetes. One (B1D4) is 96% homologous with rat muscle glycogen phosphorylase; other (B10D6) is >95% identical with human elongation factor 1α. Two clones which show moderate decreases in expression in diabetes have 100% homology with abundant muscle proteins, myosin and myoglobin. Finally, three of the differently expressed cloned show no match in the GeneBank. Two of the frequently observed "false positives" were also sequenced for information. One was identified as a Bluescript clone in which a partial duplicated β-galactosidase gene (E. coli.) was acting as an insert due to some gene rearrangement and the other as an Alu sequence.

Diabetogenes in Other Species

Diabetogenes can be isolated from other species by methods analogous to those described above. Alternatively, once a diabetogene has been isolated in a first species, e.g., in humans, it can be isolated from a second species by methods known to those skilled in the art. For example, murine Diabetogene rad can be isolated by probing a mouse cDNA or genomic library with a probe homologous to human Diabetogene rad.

Human Diabetogene rad

Clone C9D6 (isolated as described above) corresponds to a previously unknown human gene, rad. The expression of Diabetogene rad is increased in patients with NIDDM but not in patients with IDDM. Northern blot analysis of three normals, two Type I diabetics and five Type II diabetics was performed. Four of the five type II diabetics exhibit significant increases in mRNA for this interesting gene as compared to both the Type I diabetic and non-diabetic individuals. This result was reproducible in other blots.

The DNA sequence (and deduced amino acid sequence) of rad is shown in FIG. 3. (Sequence ID No. 1). The sequence of the rad gene includes an initiator codon at $Met^{122}$ and $Met^{241}$. Proteins (and DNA sequences encoding them) beginning at either site are within the invention, although it is believed that the in vivo initiation site is at $Met^{241}$. This sequence does not match any known sequence in GenBank, although one domain has some features suggestive of homology to a known transcription factor.

The cloned sequences can be expressed in an expression system to yield recombinant rad polypeptide. Antibodies, preferably more clonal antibodies directed against the Diabetogene rad protein can be made by methods known to those skilled in the art.

Other Human Diabetogenes

Several diabetogenes isolated by the methods described above correspond to known genes with known functions.

The expression of three of these. genes or sequences, muscle glycogen phosphorylase (corresponding to clone B1D4), human elongation factor 1α (corresponding to clone B10D6), and a segment of the human mitochondrial genome which codes for cytochrome oxidase and several transfer RNAs (corresponding to clone F2D8), has been shown to be elevated in Type I and Type II diabetes.

Clone B1D4 has been shown to represent human muscle glycogen phosphorylase. The mRNA for this important enzyme of glycogen metabolism is increased in skeletal muscle of both Type I and Type II diabetic patients and also increased in muscle of streptozotocin diabetic rats. Studies of the regulation of this gene in muscle cell lines (L6) in tissue culture by both insulin and glucose and will correlate these changes with protein and enzyme activity. These changes in glycogen phosphorylase may contribute to the changes in glycogen synthesis activity which are observed in diabetes.

Clone B10D6 has been identified as human elongation factor 1α (EF1α). This is a GTP binding protein which plays a critical role in the early steps of protein synthesis and ribosome formation, but whose regulation in disease has not yet been studied. In additional Northern blot analysis has been shown that the level of message is increased in muscle of individuals with both Type I and Type II diabetes between 5- and 10-fold when compared to normal. In a muscle sample from one Type I diabetic who had previously undergone pancreatic transplantation, the level of EF1α was decreased toward normal. EF1α message has also been shown to be increased in muscle and liver of streptozotocin diabetic rats but not muscle of ob/ob mice.

Clone F2D8 was previously identified to be increased in both Type I and Type II diabetes. Preliminary sequence analysis of this clone shows it to be 97% identical to a segment of the human mitochondrial genome which codes for cytochrome oxidase and several transfer RNAs. In view of the very recent description of a patient with a form of diabetes related to a defect in mitochondrial gene transmission this finding is of great interest.

Use

The peptides of the invention may be administered to a mammal, particularly a human, in one of the traditional modes (e.g., orally, parenterally, transdermally, or transmucosally), in a sustained release formulation using a biodegradable biocompatible polymer, or by on-site delivery using micelles, gels and liposomes or by transgenic modes.

OTHER EMBODIMENTS

The level of expression of one, or a combination, of diabetogenes can be used in the investigation of normal, experimentally perturbed, or disease-state metabolism. For example, the effect of a treatment, e.g., the administration of a drug, can be studied by its effect on diabetogene expression. This approach could be used to optimize or monitor treatment, or to assist in the discovery or evaluation of new treatments, e.g., of new drugs.

The effect of a treatment, e.g., the administration of a drug, could be evaluated by its effect on diabetogene mRNA or protein levels in: an animal, e.g., a human, or in an experimental animal, e.g., a transgenic animal, e.g., a transgenic animal with a mutant Diabetogene rad transgene, or an animal which is a "diabetes model", e.g., a NOD mouse, an ob/ob mouse, a db/db mouse, a Zucker fatty rat, or a streptozotocin induced rat; or a cultured cell or tissue. A useful therapy would be one which, e.g., would shift diabetogene expression in the direction of wild type.

Diabetogene expression patterns could also be used to evaluate new or existing animal-diabetes models, where a desirable model would have a predetermined pattern of diabetogene expression, e.g., a pattern which resembles that seen in a human disease state. Similarly, the effect of a mutation in a gene, e.g., a gene involved in glucose metabolism, could be studied by comparing diabetogene expression in wild type and mutant cells e.g., cell lines, or in wild type and mutant organisms.

Nucleic acid encoding a diabetogene can be used to transform cells. For example, the Diabetogene rad, e.g., a mutant form of the gene, e.g., a deletion, can be used to transform a cell and to produce a cell in which a copy of the cell's genomic Diabetogene rad has been replaced by the transformed gene, producing, e.g., a cell deleted for a copy of the gene. This approach can be used with cells capable of being grown in culture, e.g., cultured muscle cells, to investigate the function of the gene.

A diabetogene, e.g., Diabetogene rad, e.g., a mutant form of the gene, e.g., a deletion, can be used to transform a cell which subsequently gives rise to a transgenic animal. This approach can be used to create, e.g., a transgenic animal in which a copy of the gene is inactivated, e.g., by a deletion. Homozygous transgenic animals can be made by crosses between the offspring of a founder transgenic animal. Genetically altered cell lines can be made from transgenic animals. Such animals and cell lines would be useful in research.

The pattern of expression of one or a combination of diabetogenes could be used to diagnose persons at risk for diabetes or other disorders. This could be accomplished by monitoring expression of diabetogene mRNA or protein. Diabetogene rad, e.g., is more highly expressed in Type II diabetics than in Type I diabetics or in normal individuals, thus its expression could be used as a means of diagnosing risk for Type II diabetics.

Individuals at risk for a glucose-related disorder can be identified by the possession of structural defects in a diabetogene. For example, nucleic acid from an individual can be analyzed for gross chromosomal rearrangements, e.g., deletions, insertions, or translocations, or frame shifts, or point mutations at a diabetogene, by blot or sequence analysis. Even if critical diabetogenic lesions have not been characterized any gross rearrangement or any lesion which changed the reading frame of the gene would be highly likely to alter function. In the case of Diabetogene rad, any lesion likely to increase expression would be highly likely to induce a disease state.

The invention also includes preparations which inhibit the function of a diabetogene and/or its products, e.g., antibodies or antisense nucleic acids.

The invention includes the protein encoded by Diabetogene rad or any protein which is substantially homologous to Diabetogene rad or to the fragment of Diabetogene rad described in FIG. 3 (Seq ID No. 1) as well as other naturally occurring diabetogenes. Also included are: allelic variations; natural mutants; induced mutants, e.g., in vitro induced deletions; proteins encoded by DNA that hybridizes under high or low (e.g., washing at 2×SSC at 40 C with a probe length of at least 40 nucleotides) stringency conditions to a nucleic acid naturally occurring (for other definitions of high and low stringency see Current Protocols in Molecular Biology, John Wiley & Sons, New York, 1989, 6.3.1–6.3.6, hereby incorporated by reference); and polypeptides or proteins specifically bound by antisera to the Diabetogene rad protein, especially by antisera to the active site or binding domain of the Diabetogene rad protein. The term also includes chimeric polypeptides that include the Diabetogene rad protein.

The invention also includes any biologically active fragment or analog of the Diabetogene rad protein. By "biologically active" is meant possessing any in vivo or in vitro activity which is characteristic of the Diabetogene protein.

Preferred analogs include Diabetogene rad analogs (or biologically active fragments thereof) whose sequences differ from the wild-type sequence only by conservative amino acid substitutions, for example, substitution of one amino acid for another of the same class (e.g., valine for glycine, arginine for lysine, etc.) or by one or more non-conservative amino acid substitutions, deletions, or insertions which do not destroy the polypeptide's biological activity. Preferred analogs also include Diabetogene rad proteins (or biologically active fragments thereof) which are modified for the purpose of increasing peptide stability; such analogs may contain, for example, one or more desaturated peptide bonds or D-amino acids in the peptide sequence.

Analogs can differ from naturally occurring Diabetogene rad protein by amino acid sequence differences or by modifications that do not affect sequence, or by both. Analogs of the invention will generally exhibit at least 70%, more preferably 80%, more preferably 90%, and most preferably 95% or even 99%, homology with all or part of a naturally occurring Diabetogene rad protein sequence. The length of comparison sequences will generally be at least about 20 amino acid residues, preferably more than 40 amino acid residues. Modifications include , or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps, e.g., by exposing the polypeptide to glycosylation affecting enzymes derived from cells that normally provide such processing, e.g., mammalian glycosylation enzymes. Also embraced are versions of the same primary amino acid sequence that have phosphorylated amino acid residues, e.g., phosphotyrosine, phosphoserine, or phosphothreonine. Analogs can differ from naturally occurring Diabetogene rad protein by alterations of their primary sequence. These include genetic variants, both natural and induced. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule.

In addition to substantially full-length polypeptides, the invention also includes biologically active fragments of the polypeptides. As used herein, the term "fragment", as applied to a polypeptide, will ordinarily be at least about 10 contiguous amino acids, typically at least about 20 contiguous amino acids, more typically at least about 30 contiguous amino acids, usually at least about 40 contiguous amino acids, preferably at least about 50 contiguous amino acids, and most preferably at least about 60 to 80 or more contiguous amino acids in length. Fragments of Diabetogene rad protein can be generated by methods known to those skilled in the art. The ability of a candidate fragment to exhibit a biological activity of Diabetogene rad protein can be assessed by methods known to those skilled in the art. Also included are Diabetogene rad protein polypeptides containing amino acids that are normally removed during protein processing, including additional amino acids that are not required for the biological activity of the polypeptide, or including additional amino acids that result from alternative mRNA splicing or alternative protein processing events.

The invention also includes nucleic acids which encode the polypeptides of the invention.

SEQUENCE LISTING (1) GENERAL INFORMATION:

(iii) NUMBER OF SEQUENCES:   1

(2) INFORMATION FOR SEQ ID NO:   1:

(i) SEQUENCE CHARACTERISTICS:
      (A) LENGTH:     1443
      (B) TYPE:       nucleic acid
      (C) STRANDEDNESS: single
      (D) TOPOLOGY:   linear (xi) SEQUENCE DESCRIPTION: SEQ ID NO: 1:

```
GTGGCTGCAG CAGCAGCGGC GGCGGAAACC CTAAAGTCCG AGTCCGGACT ACGAGTGCGT        60

GGCCTCCTAA TCCGGATCCT AGTCCTGAGC GTGTCTGTGT GCGAGTGGAC GGTCCCGGAC       120

GCG                                                                    123

ATG ACC CTG AAC GGC GGC GGC AGC GGA GCG GGC GGG AGC CGC GGT GGG        171
met thr leu asn gly gly gly ser gly ala gly gly ser arg gly gly
 1               5                  10                  15

GGC CAG GAG CGC GAG CGC CGT CGG GGC AGC ACA CCC TGG GGC CCC GCC        219
gly gln glu arg glu arg arg arg gly ser thr pro trp gly pro ala
            20                  25                  30

CCG CCG CTG CAC CGC CGC AGC ATG CCG GTG GAC GAG CGC GAC CTG CAG        267
pro pro leu his arg arg ser met pro val asp glu arg asp leu gln
        35                  40                  45

GCG GCG CTG ACC CCG GGT GCC CTG ACG GCG GCC GCG GCC GGG ACG GGG        315
ala ala leu thr pro gly ala leu thr ala ala ala ala gly thr gly
    50                  55                  60

ACC CAG GGT CCC AGG CTG GAC TGG CCC GAG GAC TCC GAG GAC TCG CTC        363
thr gln gly pro arg leu asp trp pro glu asp ser glu asp ser leu
65                  70                  75                  80

AGC TCA GGG GGC AGC GAC TCA GAC GAG AGC GTT TAC AAG GTG CTG CTG        411
```

| | | | | | | | | | | | | |
|---|---|---|---|---|---|---|---|---|---|---|---|---|
| ser | ser | gly | gly | ser | asp | ser | asp | glu | ser | val | tyr | lys | val | leu | leu |
| | | | | 85 | | | | 90 | | | | 95 | |

```
CTG GGG GCG CCC GGC GTG GGC AAG AGC GCC CTG GCG CGC ATC TTC GGC       459
leu gly ala pro gly val gly lys ser ala leu ala arg ile phe gly
            100                 105                 110

GGT GTG GAG GAC GGG CCT GAA GCA GAG GCA GCA GGG CAC ACC TAT GAT       507
gly val glu asp gly pro glu ala glu ala ala gly his thr tyr asp
        115                 120                 125

CGC TCC ATT GTA GTG GAC GGA GAA GAG GCA TCA CTC ATG GTC TAC GAC       555
arg ser ile val val asp gly glu glu ala ser leu met val tyr asp
130                 135                 140

ATT TGG GAG CAG GAC GGG GGC CGC TGG TTG CCC GGC CAC TGC ATG GCC       603
ile trp glu gln asp gly gly arg trp leu pro gly his cys met ala
145                 150                 155                 160

ATG GGG GAT GCC TAT GTC ATT GTG TAC TCA GTG ACG GAC AAG GGC AGC       651
met gly asp ala tyr val ile val tyr ser val thr asp lys gly ser
                165                 170                 175

TTC GAG AAG GCC TCA GAA CTG CGG GTC CAG CTG CGG CGT GCA CGG CAA       699
phe glu lys ala ser glu leu arg val gln leu arg arg ala arg gln
            180                 185                 190

ACA GAT GAT GTG CCC ATC ATC CTC GTG GGC AAC AAG AGC GAC CTG GTG       747
thr asp asp val pro ile ile leu val gly asn lys ser asp leu val
        195                 200                 205

CGC TCT CGT GAG GTC TCG GTG GAT GAG GGC CGG GCC TGC GCG GTG GTC       795
arg ser arg glu val ser val asp glu gly arg ala cys ala val val
210                 215                 220

TTT GAC TGC AAG TTC ATT GAG ACA TCA GCG GCA TTG CAC CAC AAT GTC       843
phe asp cys lys phe ile glu thr ser ala ala leu his his asn val
225                 230                 235                 240

CAG GCG CTG TTT GAA GGT GTC GTG CGC CAG ATA CGC CTG CGC AGG GAC       891
gln ala leu phe glu gly val val arg gln ile arg leu arg arg asp
                245                 250                 255

AGC AAA GAA GCC AAC GCA CGA CGG CAA GCA GGC ACC CGG AGG CGA GAG       939
ser lys glu ala asn ala arg arg gln ala gly thr arg arg arg glu
            260                 265                 270

AGC CTT GGC AAA AAG GCG AAG CGC TTC TTG GGC CGC ATC GTA GCT CGT       987
ser leu gly lys lys ala lys arg phe leu gly arg ile val ala arg
        275                 280                 285

AAC AGC CGC AAG ATG GCC TTT CGC GCC AAA TCC AAG TCC TGC CAC GAC      1035
asn ser arg lys met ala phe arg ala lys ser lys ser cys his asp
290                 295                 300

CTC TCG GTT CTC TAG                                                  1050
leu ser val leu
305

GTCCCACCCG CTCCCACTAT GGTGGGAGAC GAACGGAAGG GTTGGTGGGC TGGCCCAGCC    1110

AACTGCCCCG GGTGCCTCAG AGCAGGCTCA GACTCTGGGT CCCTCGGAGC TGCCAGCCGG    1170

GCACCCCCAA CCTCATGGTC ATGGACAGAT AGACAGTGCT GCCCTGCGAA GTGGCTCTCA    1230

GGGGCCAGTG AGGGCTGGGC CCACAGAGAT GCATGCGCAG GCTCATATGC GTCCCAAGCA    1290

GCCGCAGCGC AGCCGCCGGG CAGGCCTGCG TGCCGGGAGA GGACTCTGCC TTTTTTCACA    1350

GCCCGGGTGT GCCTGCCCTG GAGGGAGGCT CTTCAGTGCG GTAGCTACTT GTTTACATGC    1410

AGATTTTTGT AATAAAGGCT ATTTCCTGAT AAA                                 1443
```

Other embodiments are within the following claims.

What is claimed is:

1. A method for determining if a test subject is at risk for Type I or Type II diabetes, comprising: examining said test subject for the expression of a gene selected from the group consisting of a muscle glycogen phosphorylase gene and a human elongation factor 1α gene, and comparing the expression of said gene in the test subject to the expression of said gene in a non-diabetic subject, wherein increased expression of said gene in the test subject is indicative of risk for Type I or Type II diabetes.

2. A method for determining if a test subject is at risk for Type II diabetes comprising examining said test subject for the expression of a a rad nucleic acid, wherein said rad nucleic acid comprises SEQ ID NO: 1 or a naturally occurring allelic variant thereof, wherein increased expression of the rad nucleic acid in the test subject as compared to expression of the rad nucleic acid in a non-diabetic subject is indicative of a risk for Type II diabetes.

3. A method for determining if a test subject is at risk for Type II diabetes comprising examining said test subject for the expression of a gene selected from the group consisting of a myosin gene, and a myoglobin gene, wherein decreased expression of the gene in the test subject as compared to expression levels of the gene in a non-diabetic subject is indicative of a risk of Type II diabetes.

4. A method for determining if a test subject is at risk for Type I diabetes comprising examining said test subject for the expression of a gene selected from the group consisting of a muscle glycogen phosphorylase gene, and a human elongation factor 1α gene, wherein increased expression of the gene in the test subject as compared to expression of the gene in a non-diabetic subject is indicative of a risk for Type I diabetes.

5. The method of claim 1, wherein the gene is a muscle glycogen phosphorylase gene.

6. The method of claim 1, wherein the gene is a human elongation factor 1α gene.

7. The method of claim 3, wherein the gene is a myosin gene.

8. The method of claim 3, wherein the gene is a myoglobin gene.

9. The method of claim 1, wherein the step of comparing the expression of said gene in the test subject to the expression of said gene in the non-diabetic subject comprises comparing mRNA expression levels of said gene.

10. The method of claim 1, wherein the step of comparing the expression of said gene in the test subject to the expression of said gene in the non-diabetic subject comprises comparing expression levels of a protein encoded by said gene.

11. The method of claim 2, wherein the step of examining said test subject for the expression of the rad nucleic acid comprises comparing mRNA expression levels of the rad nucleic acid in said test subject with mRNA expression levels of the rad nucleic acid in the non-diabetic subject.

12. The method of claim 2, wherein the step of examining said test subject for the expression of the rad nucleic acid comprises comparing expression levels of a protein encoded by the rad nucleic acid in said test subject to levels of the protein encoded by the rad nucleic acid in the non-diabetic subject.

13. The method of claim 3, wherein the step of examining said test subject for the expression of a gene selected from the group consisting of a myosin gene, and a myoglobin gene comprises comparing mRNA expression levels of the gene in the test subject to mRNA expression levels of the gene in the non-diabetic subject.

14. The method of claim 3, wherein the step of examining said test subject for the expression of a gene selected from the group consisting of a myosin gene, and a myoglobin gene comprises comparing expression levels of a protein encoded by the gene in the test subject to levels of the protein encoded by the gene in the non-diabetic subject.

* * * * *